(12) United States Patent
Livesay et al.

(10) Patent No.: US 10,586,622 B2
(45) Date of Patent: Mar. 10, 2020

(54) SYSTEMS AND METHODS FOR PREDICTING HEALTHCARE OUTCOMES BASED ON SEMANTIC RELATIONSHIPS

(71) Applicant: Michigan Health Information Network Shared Services, East Lansing, MI (US)

(72) Inventors: Jeff Livesay, Pinckney, MI (US); Tim Pletcher, Mount Pleasant, MI (US)

(73) Assignee: Michigan Health Information Network Shared Services, East Lansing, MI (US)

( * ) Notice: Subject to any disclaimer, the term of this patent is extended or adjusted under 35 U.S.C. 154(b) by 0 days.

(21) Appl. No.: 15/847,506

(22) Filed: Dec. 19, 2017

(65) Prior Publication Data

US 2019/0189287 A1 Jun. 20, 2019

(51) Int. Cl.
*G16H 50/70* (2018.01)
*G16H 10/60* (2018.01)
*G06F 16/33* (2019.01)
*G16H 50/20* (2018.01)

(52) U.S. Cl.
CPC ......... *G16H 50/70* (2018.01); *G06F 16/3344* (2019.01); *G16H 10/60* (2018.01); *G16H 50/20* (2018.01); *G06F 2216/03* (2013.01)

(58) Field of Classification Search
None
See application file for complete search history.

(56) References Cited

U.S. PATENT DOCUMENTS

| | | | |
|---|---|---|---|
| 5,155,802 A | 10/1992 | Mueller et al. | |
| 5,804,373 A | 9/1998 | Schweitzer et al. | |
| 8,605,089 B1* | 12/2013 | Heckerman | G06T 11/206 345/440 |
| 2006/0173672 A1* | 8/2006 | Bergeron | G06F 17/27 704/9 |
| 2007/0078856 A1* | 4/2007 | Dettinger | G16H 10/60 |
| 2014/0297642 A1* | 10/2014 | Lum | G06F 19/36 707/737 |
| 2014/0330929 A1* | 11/2014 | Dong | A61B 5/0022 709/217 |
| 2015/0100661 A1* | 4/2015 | Heise | H04L 47/125 709/213 |
| 2017/0255697 A1* | 9/2017 | Morris | G16H 10/60 |

* cited by examiner

*Primary Examiner* — Jonathan Ng
*Assistant Examiner* — Rachelle L Reichert
(74) *Attorney, Agent, or Firm* — Honigman LLP

(57) ABSTRACT

This disclosure provides systems and methods for predicting healthcare outcomes based on semantic relationships. An active care relationship management system can be configured to receive healthcare information. The system can update a semantic network based on the received health information. The system can evaluate the semantic network to predict a health outcome for a first patient. The system can provide an alert to the first patient or a first provider.

18 Claims, 3 Drawing Sheets

SYSTEMS AND METHODS FOR PREDICTING HEALTHCARE OUTCOMES BASED ON SEMANTIC RELATIONSHIPS

BACKGROUND

A large volume of medical information is required to provide quality healthcare to patients. For example, information relating to a patient's diagnosed conditions, prescribed treatments, treating providers, medical procedures undergone, and other information must be accurately recorded in order to provide ongoing healthcare to the patient in a safe and effective manner. However, obtaining and maintaining such information can be challenging.

SUMMARY

At least one aspect of this disclosure is directed to a system for analyzing health patterns. The system can include an event detection module configured to receive healthcare information. The system can include a network update module configured to update a semantic network based on the received healthcare information. The semantic network can include a plurality of nodes and a plurality of edges. The plurality of nodes can correspond to respective entities of a healthcare system represented by the semantic network including at least a plurality of patients, a plurality of providers, and a plurality of health organizations. Each edge can couple a respective pair of the plurality of nodes and can represent a relationship between the entities represented by the pair of nodes. The system can include a network evaluation module configured to evaluate the semantic network to identify a health pattern. The system can include an alert generation module configured to provide an alert corresponding to the identified health pattern to at least one of a first patient of the plurality of patients, a first provider of the plurality of providers, and a first health organization of the plurality of health organizations.

In some implementations, the network update module can be further configured to store, in a database, metadata associated with at least one node of the plurality of nodes. The metadata can correspond to a relationship represented by an edge coupled to the at least one node. In some implementations, the metadata can include information corresponding to a strength of the relationship represented by the edge coupled to the at least one node. In some implementations, the network update module can be further configured to modify the information corresponding to the strength of the relationship represented by the edge coupled to the at least one node, based on a response to the alert received from at least one of the first patient, the first provider, and the first health organization.

In some implementations, the network evaluation module can be further configured to identify a first subnetwork of the semantic network including a first node representing the first patient. The network evaluation module can be configured to identify a second subnetwork of the semantic network including a second node representing a second patient of the plurality of patients. The network evaluation module can be configured to determine a similarity between the first subnetwork and the second subnetwork. The network evaluation module can be configured to determine the health pattern based on the similarity between the first subnetwork and the second subnetwork.

In some implementations, the network evaluation module can be further configured to identify a landmark of the semantic network including a first node representing the first patient and at least two additional nodes of the plurality of nodes. In some implementations, the landmark can represent a patient care team including two or more providers who have provided healthcare to the first patient.

In some implementations, the system can be further configured to store at least one rule indicating a subset of the plurality of providers and the plurality of health organizations authorized to receive medical information for the first patient. The alert generation module can be further configured to provide the alert to the subset of the plurality of providers and the plurality of health organizations authorized to receive the medical information for the first patient, responsive to determining that the identified health pattern relates to the first patient.

In some implementations, the event detection module can be further configured to determine whether the semantic network should be updated based on the received healthcare information. The network update module can be further configured to update the semantic network based on a determination by the event detecting module that the semantic network should be updated. In some implementations, at least one node of the plurality of nodes of the semantic network can correspond to a treatment prescribed to the first patient.

Another aspect of this disclosure is directed to a method for analyzing health patterns. The method can include receiving, by an event detection module, healthcare information. The method can include updating, by a network update module, a semantic network based on the received healthcare information. The semantic network can include a plurality of nodes and a plurality of edges. The plurality of nodes can correspond to respective entities of a healthcare system represented by the semantic network including at least a plurality of patients, a plurality of providers, and a plurality of health organizations. Each edge can couple a respective pair of the plurality of nodes and can represent a relationship between the entities represented by the pair of nodes. The method can include evaluating, by a network evaluation module, the semantic network to identify a health pattern. The method can include providing, by an alert generation module, an alert corresponding to the identified health pattern to at least one of a first patient of the plurality of patients, a first provider of the plurality of providers, and a first health organization of the plurality of health organizations.

In some implementations, the method can include storing, by the network update module in a database, metadata associated with at least one node of the plurality of nodes. The metadata can correspond to a relationship represented by an edge coupled to the at least one node. In some implementations, the metadata can include information corresponding to a strength of the relationship represented by the edge coupled to the at least one node. In some implementations, the method can include modifying, by the network update module, the information corresponding to the strength of the relationship represented by the edge coupled to the at least one node, based on a response to the alert received from at least one of the first patient, the first provider, and the first health organization.

In some implementations, the method can include identifying, by the network evaluation module, a first subnetwork of the semantic network including a first node representing the first patient. The method can include identifying, by the network evaluation module, a second subnetwork of the semantic network including a second node representing a second patient of the plurality of patients. The method can include determining, by the network evaluation module, a similarity between the first subnetwork and the second subnetwork. The method can include determining, by the network evaluation module, the health pattern based on the similarity between the first subnetwork and the second subnetwork.

In some implementations, the method can include identifying, by the network evaluation module, a landmark of the semantic network comprising a first node representing the first patient and at least two additional nodes of the plurality of nodes. In some implementations, the landmark can represent a patient care team including two or more providers who have provided healthcare to the first patient.

In some implementations, the method can include storing at least one rule indicating a subset of the plurality of providers and the plurality of health organizations authorized to receive medical information for the first patient. The method can also include determining that the identified health pattern relates to the first patient. The method can also include providing, by the alert generation module, the alert to the subset of the plurality of providers and the plurality of health organizations authorized to receive the medical information for the first patient, responsive to determining that the identified health pattern relates to the first patient.

In some implementations, the method can include determining, by the event detection module, whether the semantic network should be updated based on the received healthcare information. The method can also include updating, by the network update module, the semantic network based on a determination by the event detecting module that the semantic network should be updated. In some implementations, at least one node of the plurality of nodes of the semantic network corresponds to a treatment prescribed to the first patient.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing.

DETAILED DESCRIPTION

Figure 1:
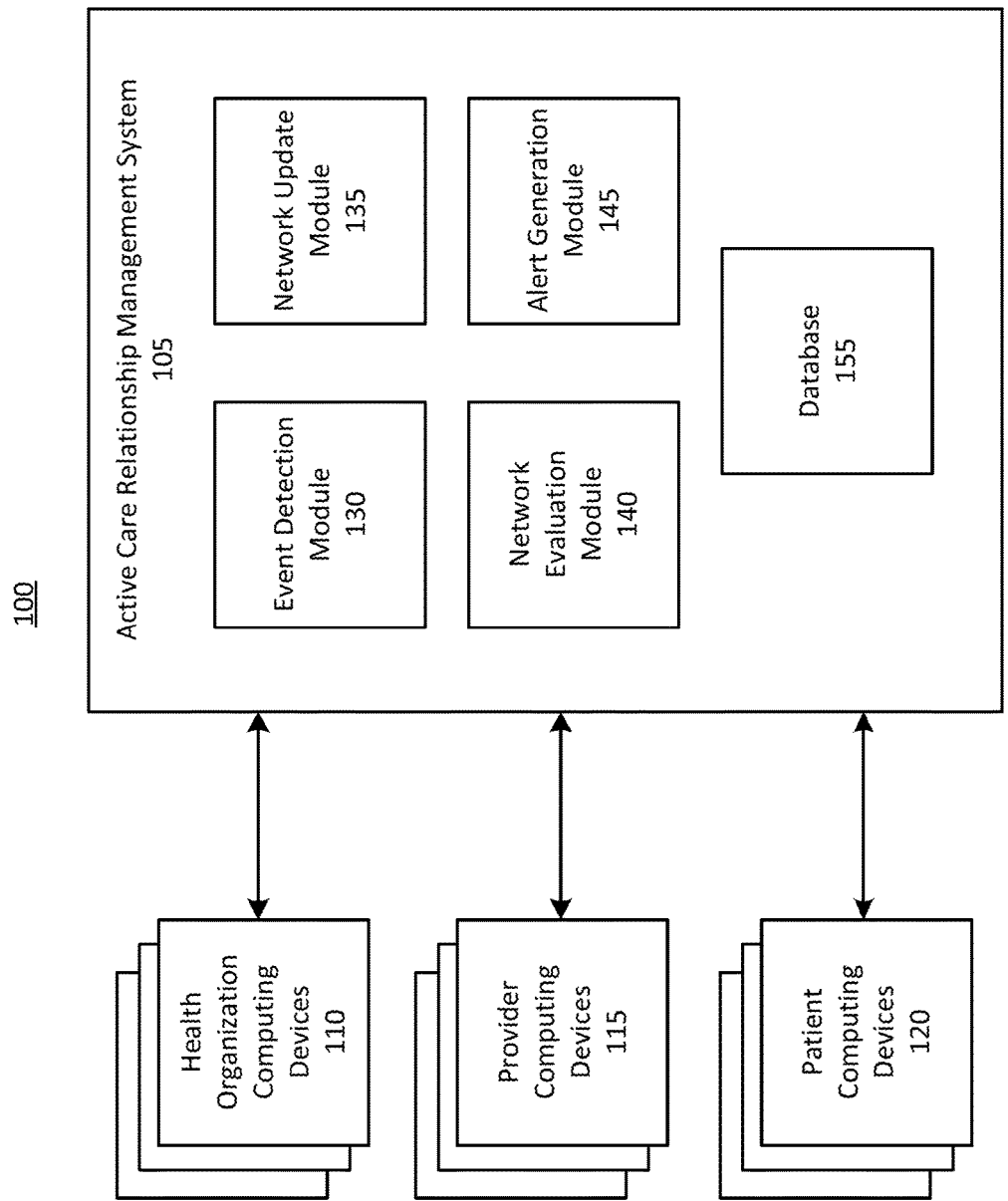
FIG. 1 illustrates an example system for collecting, maintaining, and updating medical information, according to an illustrative implementation.

Following below are more detailed descriptions of various concepts related to, and implementations of systems and methods for predicting healthcare outcomes based on semantic relationships. The various concepts introduced above and discussed in greater detail below may be implemented in any of numerous ways, as the described concepts are not limited to any particular manner of implementation. Examples of specific implementations and applications are provided primarily for illustrative purposes.

As described above, in the healthcare field a large volume of medical information is required in order to provide quality healthcare to patients. Information relating to a patient's diagnosed conditions, prescribed treatments, treating providers, medical procedures undergone, and other information must be known in order to provide ongoing healthcare to the patient in a safe and effective manner. However, obtaining and maintaining such information can be challenging. In addition, new events involving the patient can require frequent updates to such information. For example, as the patient visits new providers, is prescribed new treatments, or experiences new health events over time, information relating to these events should be recorded and made accessible to those involved in providing ongoing healthcare to the patient, to ensure that future medical treatment is consistent with the patient's full medical history. However, the volume and complexity of such information for individual patients, and for populations of patients, makes it difficult to accurately collect, maintain, and update such information in a timely manner.

This disclosure provides systems and methods for obtaining and recording patient medical information by storing such information in the form of a semantic network. The semantic network includes nodes, which may represent patients, providers, medical insurers, hospitals, pharmacies, clinics, treatments (e.g., prescribed medications), and the like. The nodes can be connected by edges representing the relationships between nodes. Semantic information relating to the relationship between each connected pair of nodes also can be maintained. For example, an edge connecting a patient node with a provider node can indicate that the provider is responsible for the healthcare provided to the patient. An edge connecting a patient node and a medication node can indicate that the patient has a prescription for the medication. Semantic information about the nodes and edges can be stored, for example, as metadata associated with the nodes.

The semantic network can be updated over time as necessary. For example, if a patient is prescribed a new medication, a node corresponding to the new medication can be added to the network and connected to the node corresponding to the patient, and semantic information indicating that the new medication has been prescribed to the patient can be stored. In this way, the semantic network can be updated in a timely manner. In some implementations, the nodes and edges of the network can be used to predict patient health outcomes and to recommend preventive care strategies. For example, patterns in the network can be recognized and used to determine similarities between two or more patients. A first subnetwork of the semantic network including a first patient can be compared to a second subnetwork including a second patient. If the subnetworks indicate that the patients have similar medical histories (e.g., similar diagnosed conditions, treatment plans, etc.), it can be determined that the patients are likely to experience similar health outcomes. Thus, historical data represented in the semantic relationships of a first patient can be used to inform the care strategy for treating a patient currently experiencing a similar medical condition. The semantic network can therefore allow for improved predictions of health outcomes, as well as improved strategies for preventive care.

FIG. 1 illustrates an example system 100 for collecting, maintaining, and updating medical information, according to an illustrative implementation. The system 100 includes an active care relationship management (ACRM) system 105, a plurality of health organization computing devices 110, a plurality of provider computing devices 115, and a plurality of patient computing devices 120. The ACRM system 110 includes an event detection module 130, a network update module 135, a network evaluation module 140, an alert generation module 145, and a database 155.

The ACRM system 105 is configured to assist with the collection and maintenance of patient medical information, and to facilitate the use of such information to predict health outcomes for individual patients or patient populations. For example, the ACRM system 105 can receive medical information from the health organization computing devices 110, the provider computing devices 115, and the patient computing devices 120, and can process the received information to determine relationships between various entities, including patients, physicians, and other healthcare providers.

In some implementations, the health organization computing devices 110 can be any type or form of computing device owned, operated, or otherwise accessed by a health organization, such as a health system, a hospital, a health plan, a medical insurer, a prescription benefit manager, a pharmacy, or a clinic. In some arrangements, each of the health organization computing devices 110 is implemented as at least one of a server, a desktop computer, or a laptop computer. In some other arrangements, each of the health organization computing devices 110 is a mobile computing device such as a tablet computing device, or a handheld computing device, such as a smartphone that can be accessed by an employee or other representative of the respective health organization.

Similarly, the provider computing devices 115 and the patient computing devices 120 may also be any type or form of computing device owned, operated, or otherwise accessed by a provider or a patient, respectively. In general, a provider can include a physician, a pharmacist, or any other person or group of people that provides healthcare to patients. In some arrangements, the provider computing devices 115 and the patient computing devices 120 can be implemented as at least one of a server, a desktop computer, a laptop computer, a tablet computing device, or a handheld computing device.

Figure 2:
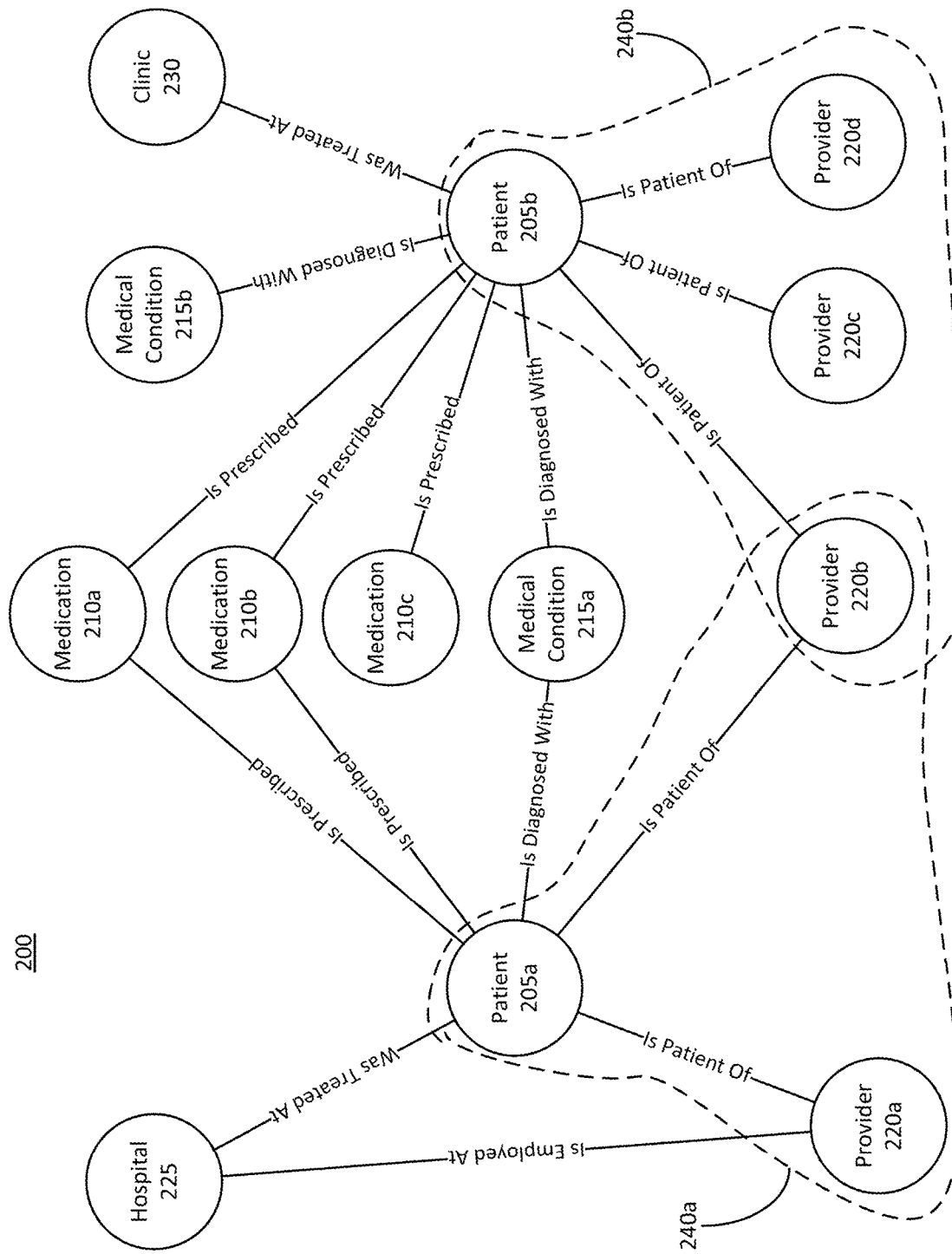
FIG. 2 illustrates an example semantic network that can be maintained by the system of FIG. 1, according to an illustrative implementation.

The ACRM system 105 can generate and continuously update a semantic network based on the information received from the health organization computing device 110, the provider computing device 115, and the patient computing device 120. An example of such a semantic network is illustrated by the semantic network 200 shown in FIG. 2. FIGS. 1 and 2 are described together below.

Referring to FIG. 2, the network 200 includes nodes represented by circles, which are connected by edges represented by solid lines. For example, nodes of the network 200 include patients 205a and 205b, medications 210a-210c, medical conditions 215a and 215b, providers 220a-220d, a hospital 225, and a clinic 230. The network 200 also includes semantic information for each edge of the network 200, as shown by the respective label for each edge. Together, the nodes and edges of the network 200, along with semantic information, represent relationships that exist among a variety of entities involved in the delivery of healthcare to the patients 205a and 205b. It should be understood that the network 200 is illustrative only, and that in practice the semantic network maintained by the ACRM system 105 may be substantially more complex. For example, the ACRM system 105 may maintain a network similar to the network 200 having hundreds, thousands, or millions of nodes, each connected by any number of edges. It should also be understood that the types of nodes and the types of semantic information shown in the network 200 are illustrative only, and are not intended to be limit the scope of this disclosure. For example, the ACRM system 105 may maintain a network similar to the network 200 having nodes corresponding to various types of treatments, health organizations, demographic information, and any other types of information that may be relevant to the healthcare of a patient or a population.

As described above, the ACRM system 105 can build and update the network 200 based on information received from the health organization computing devices 110, the provider computing devices 115, and the patient computing devices 120. In some implementations, construction and updating of the network 200 are carried out by the event detection module 130 and the network update module 135. For example, the event detection module 130 can parse the information received from the health organization computing devices 110, the provider computing devices 115, and the patient computing devices 120, and can determine whether such information constitutes an event necessitating an update to the network 200. Such events include any event that adds, removes, or alters a relationship between existing nodes in the network 200, or that adds, removes, or alters the nodes themselves. For example, a provider could use a provider computing device 115 to transmit information to the ACRM system 105 indicating that the provider is treating a particular patient, and the event detection module 130 can determine that such information should be used to update the network 200 to reflect the new provider-patient relationship.

The network update module 135 can then add a respective node corresponding to either the provider or the patient to the network 200 if such nodes are not already present in the network, and can add or modify an edge of the graph to connect these nodes. The network update module 135 also can store semantic information for the connecting edge indicating the relationship. An example of this is illustrated by the node representing the patient 205a and the provider 220a of the network 200, which are connected by an edge indicating that the patient 205a is a patient of the provider 220a. In some implementations, the network update module 135 can store information corresponding to the nodes and the edges of the graph in the database 155, and can add or modify such information over time according to events determined by the event detection module 130. Thus, as depicted in FIG. 2, the current state of the network 200 indicates that patient 205a is prescribed medications 210a and 210b, is diagnosed with medical condition 215a, is a patient of providers 220a and 220b, and was treated at hospital 225. Similarly, the network 200 also indicates that patient 205b is prescribed medications 210a, 210b, and 210c, is diagnosed with medical conditions 215a and 215b, is a patient of providers 220b, 220c, and 220d, and was treated at clinic 230.

In some implementations, the network update module 135 also can update the network 200 to include additional information. For example, the network update module 135 can update the network 200 to include metadata indicative of a strength of each relationship represented by an edge in the network 200. The strength of a relationship can indicate a confidence level that the relationship is accurate. In one example, the event detection module 130 also can parse information received from the health organization computing devices 110, the provider computing devices 115, and the patient computing devices 120 to determine multiple events indicative of a single relationship represented in the network 200. For instance, the event detection module 130 can receive information from a provider computing device 115 owned by provider 220 indicating that he or she provides healthcare to patient 205a. The event detection module 130 also can receive information from a patient computing device 120 owned by patient 205a indicating that patient 205a has received healthcare from provider 220a. In this example, the network update module 135 may determine a relatively high value for the strength of the relationship between patient 205a and provider 220a, because two separate events determined by the event detection module 130 both indicated the existence of the relationship.

Other factors also may impact the strength of a relationship in the network 200. In some implementations, the time since the network update module 135 updated the network 200 to reflect a relationship may impact the strength of the relationship. For example, if the relationship linking the patient 205a to the provider 220b is relatively old, the network update module 135 can update the network 200 to reflect a relatively lower strength of that relationship. Similarly, if the relationship between the patient 205a and the medication 210a is old, the network update module 135 can update the network 200 to reflect a lower strength of the "is prescribed" relationship between these two nodes. This can account for the increasing likelihood that the prescription has expired as time passes. In some implementations, the network update module 135 can be configured to periodically decrease the strength of a relationship in the absence of any event determined by the event detection module 130 indicating that the relationship still exists.

In some implementations, the network evaluation module 140 can analyze the network 200 to make inferences that may be relevant to the healthcare of one or more patients represented by nodes in the network 200. For example, the network evaluation module 140 can use the "is patient of" relationships in the network 200 to determine the subset of providers that should be notified of" any medical event involving a given patient. Thus, if patient 205a experiences a medical event, the network evaluation module 140 can determine that providers 220a and 220b should be notified of the event, because the graph 200 indicates that patient 205 is a patient of both of these providers. Likewise, the network evaluation module 140 can determine that providers 220c and 220d should not be notified of the event, because they do not have a connection to patient 205a. In some implementations, the network evaluation module 140 can use such information to create a set of policies or rules indicating the health organizations or providers who should be given access to medical data for each patient represented in the network 200.

In some implementations, the network evaluation module 140 can be configured to recognize patterns in subnetworks of the network 200 that can be used to predict healthcare outcomes or to select preventive care strategies for patients. For example, the network evaluation module 140 can analyze the network 200 to determine patients having similar medical histories, and can use the information relating to one patient to inform the healthcare strategy for a similar patient. As an example, in the network 200, the network evaluation module 140 can recognize that patient 205a and patient 205b are similar in that they are both diagnosed with medical condition 215a, and that they both are prescribed medication 210a and 210b. Thus, the network evaluation module 140 can determine that health outcomes relating to medical condition 215a are likely to be similar for both patients 205a and 205b. In some implementations, the network evaluation module 140 also can make inferences based on the differences between patient 205a and 205b. For example, if patient 205b experiences a good health outcome with respect to medical condition 215a, the network evaluation module 140 can recommend that patient 205a be treated in a similar manner in order to achieve a similar result. Thus, the network evaluation module 140 can identify health patterns between two patients (or between two non-patient entities represented in the semantic network 200) based on only a partial match between nodes. In this example, the network evaluation module 140 could recommend that patient 205a also be prescribed medication 210c, as is the case for patient 205b. In this way, the network evaluation module 140 can match patterns found in subnetworks of the network 200 to predict health outcomes or to recommend preventive care strategies that are likely to be effective based on the matching patterns. In addition, these patterns may be useful for identifying patients or populations of patients that may be at risk for a particular medical condition. For example, patients whose nodes exhibit patterns similar to those patients who are connected with the node representing medical condition 215a, but do not yet exhibit symptoms of the medical condition 215a, may nevertheless be identified as at risk for the medical condition 215a. As an example illustrated by the network 200, patient 205a may be identified as at risk for medical condition 215b, due to the fact that patient 205a has a medical history similar to that of patient 205b, who is already diagnosed with medical condition 215b.

As described previously, some medical information may be subject to rules that limit or restrict those who are permitted to access the information. In some instances, patient consent may be required before such information can be provided to a particular provider or health organization. Furthermore, it may be difficult and time-consuming to obtain a patient's consent. As a result, when patient consent is not obtained in advance, it may not be possible to provide relevant information in a timely manner to providers or health organizations who treat the patient. To address this issue, the network evaluation module 140 can be configured to analyze the network 200 to identify parties (i.e., any of the providers 220) who may require consent of either of the patients 205a and 205b. Continuing with the above example, the network evaluation module 140 may determine that patient 205a is likely to experience medical condition 215b, even if patient 205a is not yet experiencing symptoms associated with medical condition 215b. As a result, the network evaluation module can also determine that providers 220a and 220b, who are known to have treated patient 205a, should receive medical information for patient 205a that may be relevant to medical condition 215b. To facilitate timely communication of such information to providers 220a and 220b, the network evaluation module 140 can determine that patient 205a should be prompted to authorize providers 220a and 220b to receive such information before patient 205a has even experienced the symptoms of medical condition 215b.

In some implementations, the network evaluation module 140 also can be used to identify landmarks within the network 200. In general, a landmark can refer to any collection of two or more nodes. For example, the network evaluation module 140 can determine a landmark corresponding to a patient and a respective care team based on the subset of providers who have relationships with the patient. In the example of FIG. 2, the network evaluation module 140 can determine a landmark 240a that includes patient 205a and the respective care team of providers 220a and 220b. Similarly, the network evaluation module 140 can determine a landmark 240b that includes patient 205b and the respective care team of providers 220b, 220c, and 220d. Furthermore, the network evaluation module 140 can determine, based on the landmarks 240a and 240b, that there is overlap between the care team assigned to patient 205a and the care team assigned to patient 205b (i.e., provider 220b is a member of the care team for both patients 205a and 205b).

Such overlap may be relevant for determining how resources are provisioned between members of various care teams, who is allowed to access medical information for a particular patient, and the like. In some implementations, the network evaluation module 140 can be configured to evaluate the network 200 in this manner to determine information that should be communicated to a patient, a provider, a health organization, or another relevant party.

It should be understood that the network evaluation module 140 also can be configured to identify different types of landmarks, as well as different levels of landmarks that may themselves consist of smaller landmarks, without departing from the scope of this disclosure. Similarly, the network evaluation module 140 can be configured to identify patterns that exist between two or more landmarks in a manner similar to that described above with respect to patterns existing between groups of individual nodes. Generally, the network evaluation module 140 can be configured to evaluate the network 200 using any suitable network evaluation technique, including by performing or executing one or more semantic queries or otherwise traversing at least a portion of the network 200 to identify a health pattern.

The alert generation module 145 can be configured to provide alerts to any of the health organization computing devices 110, the provider computing devices 115, or the patient computing devices 120. For example, an alert may be any type or form of notification sent to the health organization computing devices 110, the provider computing device 115, including an email, a text message, a phone call, or a mobile application notification. For instance, the alert generation module 145 can transmit alerts based on information determined by the network evaluation module 140. In one example, as described above, the network evaluation module 140 may determine that patient 205*a* is likely to benefit from medication 210*c*, based on a positive health outcome experienced by patient 205*b*. The alert generation module 145 can be configured to identify providers connected to patient 205*a* (i.e., providers 220*a* and 220*b* in the example of FIG. 2), and to provide an alert to these providers recommending that they prescribe medication 210*c* to patient 205*a*. The alert can be provided to the providers 220*a* and 220*b*, for example, via their respective provider computing devices 115. Similarly, the alert generation module 145 also can provide an alert directly to patient 205*a* (e.g., via the respective patient computing device 120) recommending that patient 205*a* consult with a provider about receiving a prescription for medication 210*c*.

In some implementations, the alert generation module 145 can be configured to send the alert to a provider or a health organization only upon determining that the provider or first health organization is authorized to receive such information. For example, some health information may be subject to rules designed to protect patients' privacy. Consent of a patient may be required in order to provide such information to a provider or a health organization. In some implementations, information corresponding to consent rules or policies can be stored in the database 155, and the alert generation module 145 can retrieve this information prior to sending an alert to a provider or a health organization to ensure that the provider or health organization is authorized to receive the alert.

In some implementations, the alert generation module 145 can be configured to provide an alert to a patient requesting the patient's consent to allow one or more providers or health organizations to receive access to the patient's health information. For example, if the network evaluation module 140 determines that patient 205*a*

In another example, the alert generation module 145 can be configured to provide an alert to a provider or a patient in order to potentially strengthen a relationship between them. For example, if the event detection module 130 receives information from a patient computing device 120 indicating that a particular patient is being treated by a particular provider, the alert generation module 145 can be configured to provide an alert to that provider asking the provider to confirm whether the information received from the patient computing device 120 was accurate. If the provider confirms the relationship (e.g., via a respective provider computing device 115), the network update module 135 can be configured to increase a strength of the identified relationship. If the provider disputes the relationship, the alert generation module 145 can be configured to decrease a strength of the identified relationship, or to remove the identified relationship entirely.

Figure 3:
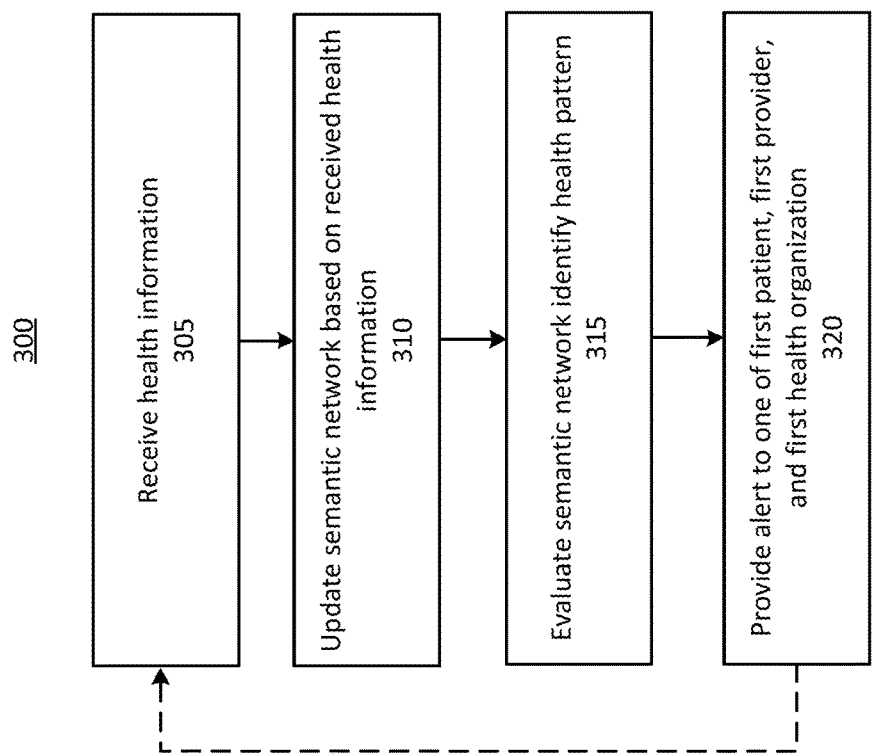
FIG. 3 illustrates a flowchart of an example method for predicting a healthcare outcome for a patient, according to an illustrative implementation.

FIG. 3 illustrates a flowchart of an example method 300 for predicting a healthcare outcome for a patient, according to illustrative implementations. In some implementations, the method 300 can be performed by the ACRM system 105 shown in FIG. 1. In brief overview, the method 300 includes receiving healthcare information (operation 305), updating a semantic network based on the received health information (operation 310), evaluating the semantic network to identify a health pattern (operation 315), and providing an alert to a first patient, a first provider, or a first health organization (operation 320).

Referring again to FIG. 3, the method 300 includes receiving healthcare information (operation 305). This operation can be performed, for example, by the event detection module 130 shown in FIG. 1. In some implementations, the healthcare information can be received from any combination of health organizations, providers, or patients. The network update module 135 can parse the received information to identify an event that necessitates an update to a semantic network that maintains information corresponding to relationships between patients, providers, and other entities involved in the provision of healthcare. An example of such a semantic network is illustrated in FIG. 2.

The method 300 includes updating the semantic network based on the received health information (operation 310). This operation can be performed, for example, by the network update module 135 shown in FIG. 1. In some implementations, the network update module 135 can modify the semantic network by adding a node, adding a new relationship between existing nodes, or modifying an existing relationship included in the semantic relationship.

The method 300 includes evaluating the semantic network to identify a health pattern (operation 315). This operation can be performed, for example, by the network evaluation module 140 shown in FIG. 1. The evaluation of the network can include any analysis of the network that results in an inference of a health pattern that may be relevant to the healthcare of one or more patients represented by nodes in the network. For example, the network evaluation module 140 can recognize patterns between similar subnetworks of the semantic network (e.g., patients who have experienced similar medical histories or who exhibit other similarities relevant to their medical needs). Based on such patterns, the network evaluation module 140 can predict a health outcome for a first patient whose medical history is similar to that of other patients whose health outcomes are known from the semantic network. For example, the network evaluation module 140 can predict that the first patient will experience a health outcome similar to that experienced by one or more similar patients represented in the semantic network.

In another example, the network evaluation module 140 can evaluate the network to determine whether a combination of medications prescribed to a patient may be unsafe. For example, in some instances, it may be unsafe for a patient to consume an opiate, an anxiolytic, and a muscle relaxant simultaneously. Thus, with reference to FIG. 2, the network evaluation module 140 could determine that medication 210a corresponds to an opiate, that medication 210b corresponds to an anxiolytic, and that medication 210c corresponds to a muscle relaxant. Because patient 205b has been prescribed all of the medications 210a-210c, the network evaluation module 140 can further determine that patient 205b is at risk of respiratory depression, which is known to be caused by such a combination of medications.

The method 300 includes providing an alert to at least one of a first patient, a first provider, or a first health organization (operation 320). This operation can be performed, for example, by the alert generation module 145 shown in FIG. 1. The alert may be provided in the form of an email, a text message, a phone call, or a mobile application notification that may be transmitted to a computing device of the first patient, the first provider, or the first health organization. In general, the alert may include information relating to the identified health pattern. For example, the alert may include a recommendation of a medical procedure or medication that should be administered to the first patient in order to achieve a successful health outcome predicted by the identified health pattern. In some other implementations, the alert may include an indication that the first patient may be at risk for a particular medical condition, for example as a result of being prescribed a predetermined combination of medications that are known to be unsafe when consumed simultaneously. The alert generation module 145 can be configured to provide an alert to notify the first patient, the first provider, or the first health organization of the identified pattern. In some implementations, the network evaluation module 140 can also be configured to identify the first provider or the first health organization based on a determination that the first provider or the first health organization is connected to the first patient in the semantic network.

In some implementations, the alert generation module 145 can be configured to send the alert to the first provider or the first health organization only upon determining that the first provider or the first health organization is authorized to receive such information, for example based on one or more policies or rules stored in the database 155. In some implementations, the steps of the method 300 can be repeated one or more times, as indicated by the arrow connecting operation 320 to operation 305.

The embodiments herein may be suitably implemented on conventional computing devices, for example, computer workstations, on Internet-based applications, on optical computing devices, neural computers, biological computers, molecular computing devices, and other devices. As may be appreciated by those skilled in the art, the present invention, in short, may be implemented on any system, automaton, and/or Turing machine.

An automaton is herein described as a mechanism that is relatively self-operating and designed to follow a predetermined sequence of operations or respond to encoded instructions. A Turing machine is herein described as an abstract expression of a computing device that may be realized or implemented on an infinite number of different physical computing devices. Examples of systems, automatons and/or Turing machines that may be utilized in performing the process of the present invention include, but are not limited to: electrical computers (for example, an International Business Machines (IBM) personal computer); neuro-computers (for example, one similar to the "General Purpose Neural Computer" described in U.S. Pat. No. 5,155,802, issued to Paul H. Mueller, on Oct. 13, 1992); molecular computers (for example, one similar to the "Molecular Automata Utilizing Single or Double-Strand Oligonucleotides" described in U.S. Pat. No. 5,804,373, issued to Allan Lee Schweiter et al., on Sep. 8, 1998); biological computers (for example, one similar to the biological computer presented by Ehud Shapiro, of the Computer Science and Applied Mathematics Department at the Weizman Institute of Science (Rehovot, Israel), at the Fifth International Meeting on DNA-Based Computers); and optical computers. For purposes of simplicity, such devices hereinafter are referred to as computers, as is commonly understood in the art. But, the embodiments disclosed herein are not limited being applied to such devices and may be accomplished upon any system or collection of systems capable of providing the features and functions identified herein. For example, the embodiments disclosed herein may be applied to devices such as neuro-synaptic computers, application specific computers (or application specific integrated circuits, sometimes referred to as ASICs), software-defined hardware, domain-specific systems on a chip, processors devoted specifically to artificial intelligence-related tasks, or any computer, processor or chip with a special architecture.

It should be understood that the systems described above may provide multiple ones of any or each of those components and these components may be provided on either a standalone machine or, in some embodiments, on multiple machines in a distributed system. The systems and methods described above may be implemented as a method, apparatus or article of manufacture using programming and/or engineering techniques to produce software, firmware, hardware, or any combination thereof. In addition, the systems and methods described above may be provided as one or more computer-readable programs embodied on or in one or more articles of manufacture. The term "article of manufacture" as used herein is intended to encompass code or logic accessible from and embedded in one or more computer-readable devices, firmware, programmable logic, memory devices (e.g., EEPROMs, ROMs, PROMs, RAMs, SRAMs, etc.), hardware (e.g., integrated circuit chip, Field Programmable Gate Array (FPGA), Application Specific Integrated Circuit (ASIC), etc.), electronic devices, a computer readable non-volatile storage unit (e.g., CD-ROM, floppy disk, hard disk drive, etc.). The article of manufacture may be accessible from a file server providing access to the computer-readable programs via a network transmission line, wireless transmission media, signals propagating through space, radio waves, infrared signals, etc. The article of manufacture may be a flash memory card or a magnetic tape. The article of manufacture includes hardware logic as well as software or programmable code embedded in a computer readable medium that is executed by a processor. In general, the computer-readable programs may be implemented in any programming language, such as LISP, PERL, C, C++, C#, PROLOG, or in any byte code language such as JAVA. The software programs may be stored on or in one or more articles of manufacture as object code.

While various embodiments of the methods and systems have been described, these embodiments are exemplary and in no way limit the scope of the described methods or systems. Those having skill in the relevant art can effect changes to form and details of the described methods and systems without departing from the broadest scope of the described methods and systems. Thus, the scope of the methods and systems described herein should not be limited by any of the exemplary embodiments and should be defined in accordance with the accompanying claims and their equivalents.

What is claimed is:

1. A system for analyzing health patterns, the system comprising:
   a semantic network comprising:
      a plurality of patient nodes, each patient node representing a respective patient;
      a plurality of provider nodes, each provider node representing a respective provider;
      a plurality of treatment nodes, each treatment node representing a respective treatment;
      a plurality of medical condition nodes, each medical condition node representing a respective medical condition; and
      a plurality of edges, each edge representing a respective relationship between a respective one of the plurality of patient nodes and one of:
         a respective provider node of the plurality of provider nodes to indicate that the patient represented by the respective patient node is treated by the provider represented by the respective provider node;
         a respective treatment node of the plurality of treatment nodes to indicate that the treatment represented by the respective treatment node is prescribed to the patient represented by the respective patient node; or
         a respective medical condition node of the plurality of medical condition nodes to indicate that the patient represented by the respective patient node is diagnosed with the medical condition represented by the respective medical condition node;
   a processor in a server having programmed instructions to cause the processor to:
      receive healthcare information from a plurality of provider computing devices, each provider computing device associated with a respective one of the plurality of provider nodes of the semantic network, and the healthcare information received from each provider computing device associated with at least on one patient treated by the provider represented by the respective provider node associated with the corresponding provider computing device;
      parse the received healthcare information;
      update the semantic network based on the parsed healthcare information;
      identify a first subnetwork of the semantic network including a first patient node of the plurality of patient nodes, the first patient node representing a first patient
      identify a second subnetwork of the semantic network including a second patient node of the plurality of patient nodes, the second patient node representing a second patient, wherein the second subnetwork comprises information representing a known health outcome of the second patient;
      determine a similarity between the first subnetwork and the second subnetwork based on the first subnetwork including a first edge of the plurality of edges and the second subnetwork including a second edge of the plurality of edges, the first edge representing the respective relationship between the first patient node and a first medical condition node of the plurality of medical condition nodes, and the second edge representing the respective relationship between the second patient node and the first medical condition node;
      identify a health pattern based on the similarity between the first subnetwork and the second subnetwork, the identified health pattern indicating that the first patient and the second patient are both diagnosed with a first medical condition represented by the first medical condition node;
      determine a difference between the first subnetwork and the second subnetwork based on the second subnetwork including a first treatment node of the plurality of treatment nodes and the first subnetwork not including the first treatment node;
      generate an alert based on the identified health pattern and the determined difference between the first subnetwork and the second subnetwork, the alert recommending that a first provider treating the first patient prescribe a first treatment represented by the first treatment node included in the second subnetwork; and
      communicate the alert to a first provider computing device of the plurality provider computing devices, the first provider computing device associated with the first provider, the alert when received by the first provider computing device causing the first provider computing device to display the alert on a screen of the first provider computing device.

2. The system of claim 1, wherein the processor stores, in a database, metadata associated with at least one edge of the plurality of edges, the metadata corresponding to the respective relationship represented by the at least one edge.

3. The system of claim 2, wherein the metadata includes information corresponding to a strength of the respective relationship represented by the at least one edge.

4. The system of claim 3, wherein the processor modifies the information corresponding to the strength of the relationship represented by the at least one edge based on a response to the alert received from the first provider computing device.

5. The system of claim 1, wherein the processor identifies a landmark of the semantic network comprising the first patient node representing the first patient a first provider node representing the first provider, and a second provider node representing a second provider.

6. The system of claim 5, wherein the landmark represents a patient care team comprising the first and second providers who have provided healthcare to the first patient.

7. The system of claim 1, wherein the programmed instructions further cause the processor to, prior to communicating the alert:
   store at least one rule indicating that the first provider is authorized to receive medical information for the first patient;
   determine that the identified health pattern relates to the first patient and
   communicate the alert to the first provider computing device responsive to determining that the identified health pattern relates to the first patient.

8. The system of claim 1, wherein the programmed instructions further cause the processor to:
   determine whether the semantic network should be updated based on the parsed healthcare information; and update the semantic network based on a determination that the semantic network should be updated.

9. A method for analyzing health patterns, the method comprising:

receiving, by a processor, healthcare information from a plurality of provider computing devices;

parsing, by the processor, the healthcare information;

updating, by the processor, a semantic network based on the parsed healthcare information, the semantic network comprising:

a plurality of patient nodes, each patient node representing a respective patient;

a plurality of provider nodes, each provider node representing a respective provider;

a plurality of treatment nodes, each treatment node representing a respective treatment;

a plurality of medical condition nodes, each medical condition node representing a respective medical condition; and a plurality of edges, each edge representing a respective relationship between a respective one of the plurality of patient nodes and one of:

a respective provider node of the plurality of provider nodes to indicate that the patient represented by the respective patient node is treated by the provider represented by the respective provider node;

a respective treatment node of the plurality of treatment nodes to indicate that the treatment represented by the respective treatment node is prescribed to the patient represented by the respective patient node; or a respective medical condition node of the plurality of medical condition nodes to indicate that the patient represented by the respective patient node is diagnosed with the medical condition represented by the respective medical condition node;

identifying, by the processor, a first subnetwork of the semantic network including a first patient node of the plurality of patient nodes, the first patient node representing a first patient;

identifying, by processor a second subnetwork of the semantic network including a second patient node of the plurality of patient nodes, the second patient node representing a second patient, wherein the second subnetwork includes information representing a known health outcome of the second patient;

determining, by the processor, a similarity between the first subnetwork and the second subnetwork based on the first subnetwork including a first edge of the plurality of edges and the second subnetwork including a second edge of the plurality of edges, the first edge representing the respective relationship between the first patient node and a first medical condition node of the plurality of medical condition nodes, and the second edge representing the respective relationship between the second patient node and the first medical condition node;

identifying, by the processor, a health pattern based on the similarity between the first subnetwork and the second subnetwork, the identified health pattern indicating that the first patient and the second patient are both diagnosed with a first medical condition represented by the first medical condition node;

determining, by the processor, a difference between the first subnetwork and the second subnetwork based on the second subnetwork including a first treatment node of the plurality of treatment nodes and the first subnetwork not including the first treatment node;

generating, by the processor, an alert based on the identified health pattern and the determined difference between the first subnetwork and the second subnetwork, the alert recommending that a first provider treating the first patient prescribe a first treatment represented by the first treatment node included in the second subnetwork; and communicating, by the processor, the alert to a first provider computing device of the plurality of provider computing devices, the first provider computing device associated with the first provider, the alert when received by the first provider computing device causing the first provider computing device to display the alert on a screen of the first provider computing device.

10. The system of claim 1, wherein the first treatment represented by the first treatment node comprises at least one of a prescribed medication or a prescribed medical treatment.

11. The method of claim 9, further comprising storing, by the processor, in a database, metadata associated with at least one edge of the plurality of edges, the metadata corresponding to the respective relationship represented by the at least one edge.

12. The method of claim 11, wherein the metadata includes information corresponding to a strength of the respective relationship represented by the at least one edge.

13. The method of claim 12, further comprising modifying, by the processor, the information corresponding to the strength of the relationship represented by the at least one edge based on a response to the alert received from the first provider computing device.

14. The method of claim 9, further comprising identifying, by the processor, a landmark of the semantic network comprising the first patient node representing the first patient, a first provider node representing the first provider, and a second provider node representing, a second provider.

15. The method of claim 14, wherein the landmark represents a patient care team comprising the first and second providers who have provided healthcare to the first patient.

16. The method of claim 9, further comprising, prior to communicating the alert:

storing, by the processor, at least one rule indicating that the first provider is authorized to receive medical information for the first patient;

determining, by the processor, that the identified health pattern relates to the first patient; and communicating, by the processor, the alert to the first provider computing device responsive to determining that the identified health pattern relates to the first patient.

17. The method of claim 9, further comprising:

determining, by the processor, whether the semantic network should be updated based on the parsed healthcare information; and updating, by the processor, the semantic network based on a determination that the semantic network should be updated.

18. The method of claim 9, wherein the first treatment represented by the first treatment node comprises at least one of a prescribed medication or a prescribed medical treatment.

* * * * *